United States Patent
Ali et al.

(10) Patent No.: US 12,201,650 B1
(45) Date of Patent: Jan. 21, 2025

(54) **METHOD OF MAKING SILVER NANOPARTICLES CAPPED WITH *CARALLUMA SINAICA* EXTRACT AND TREATMENT METHOD USING THE SAME**

(71) Applicant: KING FAISAL UNIVERSITY, Al Hasa (SA)

(72) Inventors: Enas Mohamed Ali, Al Hasa (SA); Basem Mohamed Abdallah, Al Hasa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/511,152

(22) Filed: Nov. 16, 2023

(51) Int. Cl.
*A61K 33/38* (2006.01)
*A61K 36/24* (2006.01)

(52) U.S. Cl.
CPC .............. *A61K 33/38* (2013.01); *A61K 36/24* (2013.01); *A61K 2121/00* (2013.01)

(58) Field of Classification Search
None
See application file for complete search history.

(56) References Cited

U.S. PATENT DOCUMENTS

2015/0024204 A1  1/2015  Amanchi Bala et al.
2016/0128375 A1  5/2016  Isak et al.

OTHER PUBLICATIONS

Alamier, W.A., et al., Silver Nanoparticles' Biogenic Synthesis Using Caralluma subulata Aqueous Extract and Application for Dye Degradation and Antimicrobials Activities, Catalysts 2023, 13, 1290 https://doi.org/10.3390/catal13091290.*

Al-Massarani, S.M., et al., Acylated pregnane glycosides from Caralluma sinaica, Phytochemistry 79 (2012) 129-140.*

Ronavari, A., et al., Biosynthesized silver and Id nanoparticles are potent antimycotics against opportunistic pathogenic yeasts and dermatophytes, International Journal of Nanomedicine 2018: 13 695-703.*

Alamier, Waleed M., et al. "Silver Nanoparticles' Biogenic Synthesis Using Caralluma subulata Aqueous Extract and Application for Dye Degradation and Antimicrobials Activities." Catalysts 13.9 (2023): 1290.

Amrati, Fatima Ez-Sahra, et al. "Caralluma europaea (Guss.) NE BR.: Anti-inflammatory, antifungal, and antibacterial activities against nosocomial antibiotic-resistant microbes of chemically characterized fractions." Molecules 26.3 (2021): 636.

Rónavári, Andrea, et al. "Biosynthesized silver and gold nanoparticles are potent antimycotics against opportunistic pathogenic yeasts and dermatophytes." International journal of nanomedicine (2018): 695-703.

Al-Massarani, Shaza M., et al. "Acylated pregnane glycosides from Caralluma sinaica." Phytochemistry 79 (2012): 129-140.

Albalawi, Marzough Aziz Dager, et al. "Anticancer and antifolate activities of extracts of six Saudi Arabian wild plants used in folk medicine." J. Life Sci 9 (2015): 334-340.

* cited by examiner

*Primary Examiner* — H. Sarah Park

(74) *Attorney, Agent, or Firm* — Nath, Goldberg & Meyer; Joshua B. Goldberg

(57) ABSTRACT

In order to inhibit the growth of fungi, such as *Cryptococcus neoformans*, silver nanoparticles are synthesized and capped with an extract of *Caralluma sinaica*. The silver nanoparticles capped with the extract of *Caralluma sinaica* are made by adding the extract of *Caralluma sinaica* to an aqueous silver nitrate solution to reduce the silver nitrate and form a suspension of silver nanoparticles capped with the extract of *Caralluma sinaica*. The silver nanoparticles capped with the extract of *Caralluma sinaica* are removed from the suspension by centrifugation or the like. The silver nanoparticles capped with *Caralluma sinaica* extract exhibit strong antifungal activity. To treat a *Cryptococcus neoformans* infection, an effective dose of the silver nanoparticles capped with *Caralluma sinaica* extract may be administered to a patient in need thereof.

3 Claims, No Drawings

METHOD OF MAKING SILVER NANOPARTICLES CAPPED WITH *CARALLUMA SINAICA* EXTRACT AND TREATMENT METHOD USING THE SAME

BACKGROUND

Field

The disclosure of the present patent application relates to antifungal agents, and particularly to a method of making silver nanoparticles capped with *Caralluma sinaica* extract, and further to a treatment method using the silver nanoparticles capped with *Caralluma sinaica* extract to inhibit growth of fungi, such as *Cryptococcus neoformans*.

Description of Related Art

*Cryptococcus neoformans* is an encapsulated yeast belonging to the class Tremellomycetes and an obligate aerobe that can live in both plants and animals. *Cryptococcus neoformans* can cause disease in immunocompetent, as well as immunocompromised, hosts. Infection with *C. neoformans* is termed cryptococcosis. Most infections with *C. neoformans* occur in the lungs, however, fungal meningitis and encephalitis, especially as a secondary infection for AIDS patients, are often caused by *C. neoformans*, making it a particularly dangerous fungus. Infections with this fungus are rare in people with fully functioning immune systems, thus *C. neoformans* is often referred to as an opportunistic pathogen.

In human infection, *C. neoformans* is spread by inhalation of aerosolized basidiospores, and can disseminate to the central nervous system, where it can cause meningoencephalitis. In the lungs, *C. neoformans* cells are phagocytosed by alveolar macrophages. Macrophages produce oxidative and nitrosative agents, creating a hostile environment, to kill invading pathogens. However, some *C. neoformans* cells can survive intracellularly in macrophages. Intracellular survival appears to be the basis for latency, disseminated disease, and resistance to eradication by antifungal agents. One mechanism by which *C. neoformans* survives the hostile intracellular environment of the macrophage involves upregulation of expression of genes involved in responses to oxidative stress.

Due to the resistance of *C. neoformans* to traditional antifungal agents, alternative treatments are of great interest. Nanoparticles, both alone and used as carriers of antifungal agents, provide a promising avenue for treatment of *C. neoformans*. Presently, metallic nanoparticles are the most commonly used type of nanoparticles in *C. neoformans* therapy and act as both antifungal agents and drug nanocarriers. Metallic nanoparticles can eradicate microorganisms by disturbing their structure and functions. Specifically, the nanoparticles can disrupt the cell wall when positively charged ions of the nanoparticles bind to negatively charged components. This leads to the formation of pores in the cell wall, which allows cytoplasmic content to leak from the fungal cell, potentially leading to cell death.

Various metallic nanoparticles have been proposed for the targeted treatment of *C. neoformans*, including gold (Au) nanoparticles and silver (Ag) nanoparticles. Gold and silver nanoparticles have received a great deal of interest in recent years for the treatment of various types of infections. Although the gold and silver nanoparticles are somewhat effective on their own, using the nanoparticles as both treatment agents and nanocarriers for additional antifungal agents is generally viewed as a highly promising treatment for most types of *C. neoformans* infection. Since functionalizing or capping the nanoparticles with traditional antifungal agents would not be effective against *C. neoformans*, alternative agents, such as plant phytochemicals with antifungal properties, are of interest. Thus, a method of making silver nanoparticles capped with *Caralluma sinaica* extract and a treatment method using the same solving the aforementioned problems are desired.

SUMMARY

In order to inhibit the growth of fungi, such as *Cryptococcus neoformans*, as a non-limiting example, silver nanoparticles are synthesized and capped with an extract of *Caralluma sinaica*, a perennial desert succulent plant. The silver nanoparticles capped with the extract of *Caralluma sinaica* are made by adding the extract of *Caralluma sinaica* to an aqueous silver nitrate ($AgNO_3$) solution to reduce the silver nitrate and form a suspension of silver nanoparticles capped with the extract of *Caralluma sinaica*. The extract of *Caralluma sinaica* acts as a reducing and stabilizing agent while also functionalizing the surfaces of the silver nanoparticles to cap said surfaces. The silver nanoparticles capped with the extract of *Caralluma sinaica* are then removed from the suspension by centrifugation or the like, followed by washing with water and ethanol and then drying.

In order to make the extract of *Caralluma sinaica*, *Caralluma sinaica* stem is dried and pulverized to form powdered *Caralluma sinaica*. The powdered *Caralluma sinaica* is mixed into water to form a mixture, and the mixture is then boiled. The boiled mixture is cooled and subsequently blended using an electric mixer or the like. The blended mixture is filtered using filter paper or the like, and the filtrates are collected. The filtrates are heated in an oven or the like to form the extract of *Caralluma sinaica* in the form of a dried residue.

The silver nanoparticles capped with *Caralluma sinaica* extract exhibit strong antifungal activity. In order to treat a *Cryptococcus neoformans* infection, an effective dose of the silver nanoparticles capped with *Caralluma sinaica* extract may be administered to a patient in need thereof.

These and other features of the present subject matter will become readily apparent upon further review of the following specification.

DETAILED DESCRIPTION

In order to inhibit the growth of fungi, such as *Cryptococcus neoformans*, as a non-limiting example, silver nanoparticles are synthesized and capped with an extract of *Caralluma sinaica*, a perennial desert succulent plant. The silver nanoparticles capped with the extract of *Caralluma sinaica* are made by adding the extract of *Caralluma sinaica* to an aqueous silver nitrate ($AgNO_3$) solution to reduce the silver nitrate and form a suspension of silver nanoparticles capped with the extract of *Caralluma sinaica*. The extract of *Caralluma sinaica* acts as a reducing and stabilizing agent while also functionalizing the surfaces of the silver nanoparticles to cap the surfaces with the extract of *Caralluma sinaica*. The silver nanoparticles capped with the extract of *Caralluma sinaica* are removed from the suspension by centrifugation or the like.

In an embodiment, in order to make the extract of *Caralluma sinaica*, *Caralluma sinaica* stem is dried and pulverized to form powdered *Caralluma sinaica*. The powdered *Caralluma sinaica* is mixed into water to form a mixture, and the mixture is then boiled. The boiled mixture is cooled and subsequently blended using an electric mixer or the like. The blended mixture is filtered using filter paper or the like, and the filtrates are collected. The filtrates are heated in an oven or the like to form the extract of *Caralluma sinaica* in the form of a dried residue.

The silver nanoparticles capped with *Caralluma sinaica* extract exhibit strong antifungal activity. In order to treat a *Cryptococcus neoformans* infection, an effective dose of the silver nanoparticles capped with *Caralluma sinaica* extract may be administered to a patient in need thereof.

Example 1

Silver nitrate solution (0.1 M, $AgNO_3$) was prepared in Milli-Q water under dark conditions. An aqueous stem extract of *Caralluma sinaica* (0.5% w/v) was used for the reduction of silver (Ag) into the $Ag^0$ state by mixing the aqueous stem extract of *Caralluma sinaica* with 0.5 mM $AgNO_3$. The mixture of *Caralluma sinaica* extract and $AgNO_3$ was temperature controlled at 50° C. with continuous stirring. The reduction of the Ag ions in solution was monitored by a visible color change and periodic mixture sampling by measuring in the UV-visible range. The suspension was centrifuged at 13,500 rpm for 10 minutes to remove the silver nanoparticles capped with the extract of *Caralluma sinaica*, followed by washing three times with water, and a final wash with ethanol. There resultant silver nanoparticles capped with the extract of *Caralluma sinaica* were dried at 40° C. for 48 hours.

Example 2

Dried stem samples of *Caralluma sinaica* (200 g) were powdered and then added to 5 L of hot water. After 7 hours, the mixture was gradually boiled for 1 hour. The mixture was then cooled to room temperature and blended in an electric mixer for 30 minutes. The resultant blended solution was filtered using 250 mm filter papers, and the filtrates were dried in an oven at 50° C. to make the extract of *Caralluma sinaica* in the form of dried residue. The yield mean of *Caralluma sinaica* stem extract was 25.5%. The extract was stored in a refrigerator until used as the *Caralluma sinaica* extract in the method described in Example 1 above.

It is to be understood that the method of making silver nanoparticles capped with *Caralluma sinaica* extract and the treatment method using the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of treating *Cryptococcus neoformans* infection, comprising administering to a patient in need thereof an effective dose of silver nanoparticles capped with *Caralluma sinaica* extract, the silver nanoparticles capped with *Caralluma sinaica* extract prepared by a method comprising the steps of:
    drying and pulverizing a stem of *Caralluma sinaica* to form powdered *Caralluma sinaica*;
    mixing the powdered *Caralluma sinaica* into water to form a mixture;
    boiling the mixture;
    cooling the mixture to room temperature and subsequently blending the mixture;
    filtering the blended mixture and collecting filtrates therefrom;
    heating the filtrates to form the extract of *Caralluma sinaica*;
    adding the extract of *Caralluma sinaica* to an aqueous silver nitrate solution to reduce the silver nitrate and form a suspension of silver nanoparticles capped with the extract of *Caralluma sinaica*; and
    collecting the silver nanoparticles capped with the extract of *Caralluma sinaica* from the suspension.

2. The method of making silver nanoparticles capped with *Caralluma sinaica* extract as recited in claim 1, wherein the step of collecting the silver nanoparticles capped with the extract of *Caralluma sinaica* from the suspension comprises centrifuging the suspension.

3. The method of making silver nanoparticles capped with *Caralluma sinaica* extract as recited in claim 2, further comprising the steps of washing and drying the silver nanoparticles capped with the extract of *Caralluma sinaica*.

* * * * *